United States Patent [19]

Natarajan et al.

[11] 4,284,624

[45] Aug. 18, 1981

[54] MIXED DISULFIDES

[75] Inventors: Sesha I. Natarajan, Neshanic Station; Miguel A. Ondetti; Shih-jung Lan, both of Princeton; Keith K. Wong, Milltown, all of N.J.

[73] Assignee: E. R. Squibb & Sons, Inc., Princeton, N.J.

[21] Appl. No.: 146,729

[22] Filed: May 2, 1980

[51] Int. Cl.$^3$ .................. A61K 31/40; C07D 207/416
[52] U.S. Cl. ........................ 424/177; 260/112.5 R; 260/326.25; 260/326.35; 260/326.36; 260/326.42; 424/274
[58] Field of Search ............... 260/326, 42, 326.35, 260/326.36, 326.25, 112.5 R; 424/274, 177

[56] References Cited

U.S. PATENT DOCUMENTS

| | | | |
|---|---|---|---|
| 4,105,776 | 8/1978 | Ondetti et al. | 424/274 |
| 4,154,736 | 5/1979 | Ondetti | 424/274 |
| 4,154,935 | 5/1979 | Ondetti et al. | 424/274 |
| 4,154,942 | 5/1979 | Ondetti et al. | 424/274 |
| 4,154,960 | 5/1979 | Ondetti et al. | 424/274 |
| 4,192,878 | 3/1980 | Ondetti | 424/246 |

OTHER PUBLICATIONS

Wong et al., Abstract of Article Appearing in Pharmacologist, vol. 21, p. 173 (1979), The *In Vitro* Metabolism of $C^{14}$-Captopril in the Blood of Rats, Dogs and Humans.

*Primary Examiner*—Donald G. Daus
*Assistant Examiner*—M. C. Eakin
*Attorney, Agent, or Firm*—Lawrence S. Levinson; Stephen B. Davis

[57] ABSTRACT

This invention is directed to compounds of the formula

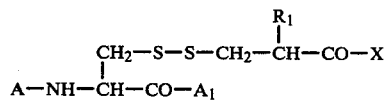

wherein A and $A_1$ are amino acid residues, X is and α-imino acid residue, and $R_1$ is hydrogen, lower alkyl, or halo substituted lower alkyl. These compounds are useful as hypotensive agents.

8 Claims, No Drawings

MIXED DISULFIDES

BACKGROUND OF THE INVENTION

Ondetti et al. in U.S. Pat. No. 4,105,776 disclose various mercaptoacyl, acylmercaptoacyl, substituted mercaptoacyl, and disulfideacyl N-substituted prolines. The proline ring can be substituted, for example, in the 4-position by a hydroxy or lower alkyl group. Ondetti et al. disclose that these compounds are useful as hypotensive agents due to their angiotensin converting enzyme inhibitory activity. Among the compounds disclosed by Ondetti et al. is captopril, 1-(D-3-mercapto-2-methylpropanoyl)-L-proline.

Wong et al., "The In Vitro Metabolism of [14]C-Captopril In The Blood of Rats, Dogs and Humans", Pharmacologist, Vol. 21, p.173 (August, 1979) identifies captopril-glutathione and captoprilcysteine mixed disulfides as metabolites of captopril.

Ondetti et al. in U.S. Pat. No. 4,154,935 disclose that various mercaptoacyl 4-halo or 4,4-halo substituted prolines and the corresponding disulfides are useful hypotensive agents.

Ondetti in U.S. Pat. No. 4,192,878 disclose that various mercaptoacyl thiazolidinecarboxylic acids are useful hypotensive agents.

Ondetti et al. in U.S. Pat. No. 4,154,942 discloses that various mercaptoacyl 3,4-dehydroprolines and that corrresponding disulfides are useful hypotensive agents.

SUMMARY OF THE INVENTION

This invention is directed to new mixed disulfides of formula I and salts thereof

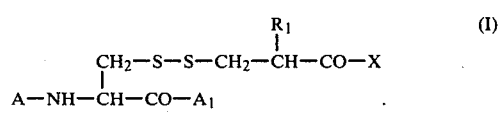

A and $A_1$ each is an amino acid residue. The amino acid represented by A is joined through a carbonyl group,

while the amino acid represented by $A_1$ is joined through an amino group, —NH—. A and $A_1$ are preferably selected from glycyl, alanyl, valyl, leucyl, α- or γ-glutamyl, α- or β-aspartyl, phenylalanyl, tyrosyl, tryptophyl, lysyl, arginyl, or prolyl.

X is a naturally occurring or synthetic α-imino acid residue joined through its N-atom. Exemplary α-imino acid residues are groups of the formulas:

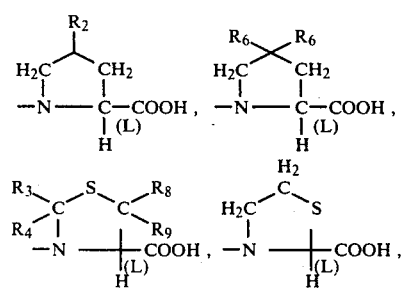

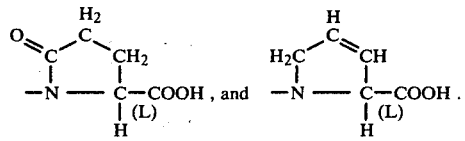

$R_1$ is hydrogen, lower alkyl, or halo substituted lower alkyl.

$R_2$ is hydrogen, hydroxy, lower alkyl, halogen, keto,

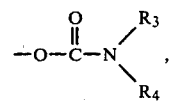

or —Y—$R_5$,

Y is O or S.

$R_5$ is lower alkyl, substituted or unsubstituted phenyl, substituted or unsubstituted phenyl-lower alkylene, substituted or unsubstituted 1- or 2-naphthyl, or substituted or unsubstituted biphenyl.

$R_6$ is halogen or —Y—$R_7$.

$R_7$ is lower alkyl, substituted or unsubstituted phenyl, substituted or unsubstituted phenyl-lower alkylene, or the $R_7$ groups join to complete an unsubstituted 5- or 6-membered ring or said ring in which one or more of the carbon atoms has a lower alkyl or di(lower alkyl) substituent.

$R_3$, $R_4$, $R_8$ and $R_9$ are independently selected from hydrogen and lower alkyl.

DETAILED DESCRIPTION OF THE INVENTION

This invention in its broadest aspect relates to the mixed disulfides of formula I above and to salts thereof, to compositions containing such compounds and to the method of using such compounds as anti-hypertensive agents.

The term lower alkyl used in the definition of the various symbols are straight or branched chain hydrocarbon radicals having up to four carbon atoms, i.e., methyl, ethyl, propyl, isopropyl, butyl, isobutyl, t-butyl. Methyl and ethyl are the preferred lower alkyl groups. Similarly, the terms lower alkoxy and lower alkylthio refer to such groups attached to an oxygen or sulfur.

The term halogen refers to chloro, bromo and fluoro and the term halo substituted lower alkyl refers to such lower alkyl groups described above in which one or more hydrogens have been replaced by chloro, bromo or fluoro groups such as trifluoromethyl, pentafluoroethyl, 2,2,2-trichloroethyl, chloromethyl, bromomethyl, etc.

The term phenyl-lower alkylene refers to groups of the formula

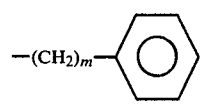

wherein m is an integer from 1 to 4. Preferred phenyl-lower alkylene groups are phenylmethyl and phenylethyl, especially phenylmethyl.

The terms substituted phenyl, substituted phenyl-lower alkylene, substituted 1- or 2-naphthyl, and substituted biphenyl include such groups having one or two, preferably one, substituent on the ring. Suitable substituents include lower alkyl groups of 1 to 4 carbons, especially methyl, lower alkoxy groups of 1 to 4 carbons, especially methoxy, lower alkylthio groups of 1 to 4 carbons, especially methylthio, halogens, especially chloro or fluoro, trifluoromethyl, acetyloxy and hydroxy. The hydroxy substituted compounds are obtained by hydrolysis of the corresponding acetyloxy substituted compound as the last step of the synthetic procedure.

Preferred compounds of this invention are those wherein $R_1$ is hydrogen, methyl or trifluoromethyl, especially methyl; A is γ-glutamyl; $A_1$ is glycyl; and X is (L)-proline, 4-hydroxy-(L)-proline, 4-methoxy-(L)-proline, 4,4-ethylenedioxo-(L)-proline, 4,4-ethylenedithio-(L)-proline, 4-phenoxy-(L)-proline, 4-phenylthio-(L)-proline, 4-(2-naphthenyloxy-(L)-proline, 4-([1,1-biphenyl]-4-yloxy)-(L)-proline, or (L)-thiazolidine-4-carboxylic acid, especially (L)-proline.

When $R_1$ is methyl or trifluoromethyl the asymmetric carbon to which $R_1$ is attached is preferably in the D-configuration. The asymmetric carbon to which

and A—NH— are attached is preferably in the L-configuration as are any other asymmetric carbons that may be present in the A and $A_1$ groups.

The compounds of formula I are obtained by reacting the 3-sulfenylphthalimido compound of the formula

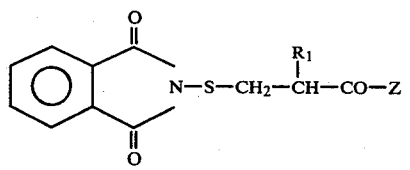

wherein Z is the benzhydryl ester of the α-imino acid residue X, with the tripeptide

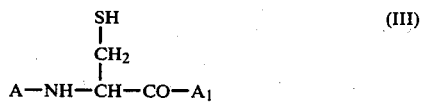

followed by treatment with trifluoroacetic acid, acetic acid, and anisole to remove the benzhydryl group. The tripeptides of formula III are prepared by procedures known in the art of peptide synthesis. See for example Methoden der Organischen Chemie(Houben Wieyl) Vol. XV, parts 1 and 2 (1974).

The 3-sulfenylphthalimido intermediate of formula II is obtained by treating the disulfide

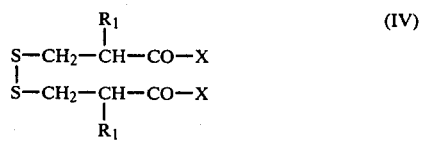

with diphenyldiazomethane to yield the ester product

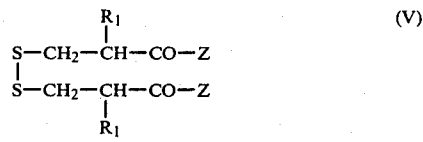

which is then reacted in an organic solvent with bromine and potassium phthalimide.

The disulfide of formula IV is obtained by directly oxidizing with iodine the mercaptoacyl compound of the formula

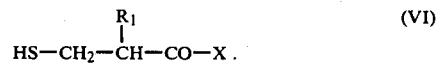

The mercaptoacyl compounds of formula VI are obtained by coupling the α-imino acid, HX, with an acid or its chemical equivalent of the formula

wherein $R_{10}$ is a hydrolyzably or chemically removable protecting group.

The disulfides of formula IV are disclosed in various patents and pending applications depending upon the definition of X. For example, those compounds wherein X is proline, 4-lower alkyl proline, or 4-hydroxyproline are disclosed by Ondetti et al. in U.S. Pat. No. 4,105,776, those compounds wherein X is mono or dihalo substituted proline are disclosed by Ondetti et al. in U.S. Pat. No. 4,154,935, those wherein X is carbamoyloxy substituted proline are disclosed by Krapcho in U.S. Ser. No. 66,119, now U.S. Pat. No. 4,217,359, those wherein X is an ether or thioether 4-substituted proline are disclosed by Ondetti et al. in U.S. Ser. No. 126,239, those wherein X is a 4-keto substituted proline are disclosed by Ondetti in U.S. Ser. No. 112,004, those wherein X is an ether or thioether 4,4-substituted proline are disclosed by Krapchlo in U.S. Ser. No. 99,164, now abandoned, those wherein X is a thiazolidine carboxylic acid are disclosed by Ondetti in U.S. Pat. No. 4,192,878, those wherein X is a 5-keto substituted proline by Ondetti et al. in U.S. Ser. No. 51,772, now U.S. Pat. No. 4,234,489, and those wherein X is a 3,4-dehydroproline are disclosed by Ondetti et al. in U.S. Pat. No. 4,154,942.

The compounds of this invention being amphoteric in nature form basic and acid addition salts with a variety of inorganic or organic bases and acids. The salt forming ion derived from such bases can be metal ions, e.g., aluminum, alkali metal ions, such as sodium or potassium, alkaline earth metal ions such as calcium or magnesium, or an amine salt ion, of which a numare known for this purpose, for example aralkylamines like, dibenzylamine, N,N-dibenzylethylenediamine, lower alkylamines like methylamine, t-butylamine, procaine, lower alkylpiperidines like N-ethylpiperidine, cycloalkylamines, like cyclohexylamine or dicyclohexylamine, 1-adamantanamine, benzathine, or salts derived from amino acid like arginine, lysine or the like. The physiologically acceptable salts like the sodium or potassium salts can be used medicinally as described below and are preferred. The acid addition salts are derived from inorganic acids such as hydrochloric or sulfuric or organic acids such as acetic, malic, maleic, succinic, tartaric, etc.

The compounds of formula I and their physiologically acceptable salts are useful as hypotensive agents. They inhibit the conversion of the decapeptide angiotensin I to angiotensin II and, therefore, are useful in relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the angiotensin→(renin)→angiotensin I→(ACE)→angiotensin II sequence by inhibiting angiotensin converting enzyme and reducing or eliminating the formation of the pressor substance angiotensin II. Thus by the administration of a composition containing one, or a combination of compounds of formula I, angiotensin dependent hypertension in the species of mammal suffering therefrom is alleviated. A single dose, or preferably two to four divided daily doses, provided on a basis of about 0.1 to 100 mg. per kilogram of body weight per day, preferably about 1 to 15 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises (for a 70 kg. mammal) a total daily dosage of about 30 to 600 mg., preferably about 30 to 300 mg., of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorthiazide, hydrochlorothiazide, flumethiazide, hydroglumethiazide, bendroflumethiazide, methchlothiazide, trichlormethiazide, polythiazide or benzthiazide, as well as ethacrynic acid, ticrynafen, chlorthalidone, furosemide, musolimine, bumetanide, triamterene, amiloride and spironolactone, and salts of such compounds.

The compounds of formula I can be formulated for use in the reduction of blood pressure in compositions such as tablets, capsules or elixirs for oral administration or in sterile solutions or suspensions for parenteral administration. About 10 to 500 mg. of a compound or mixture of compounds of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative process details are set forth in the following examples for the various reactions. These examples are preferred embodiments and also serve as models for the preparation of other compounds of this invention. The temperatures are given in degrees on the centigrade scale.

EXAMPLE 1

(S,S)-N-[3-[[3-(2-Carboxy-1-pyrrolidinyl)-2-methyl-3-oxopropyl]dithio]-N-(L-γ-glutamyl)-L-alanyl]glycine (a)

1,1'-[Dithiobis(D-2-methyl-1-oxopropane-3,1-diyl)-]bis[L-proline]

3 g. of 1-(3-mercapto-2-D-methylpropanoyl)-L-proline, prepared for example according to the procedure of Example 34 in U.S. Pat. No. 4,105,776, is dissolved in 67 ml. of water and the pH is adjusted to 6.5 with N sodium hydroxide. To this a total of 27.8 ml. of 0.5 M iodine solution (95% ethanol) is added dropwise while maintaining a pH of 5.5 to 6.5 with N sodium hydroxide. After fifteen minutes a trace of excess iodine is discharged with dilute sodium thiosulfate. The reaction mixture is concentrated in vacuo, acidified with concentrated HCl and the crystals filtered to yield 2.77 g. of 1,1'-[dithiobis(D-2-methyl-1-oxopropane-3,1-diyl)-]bis[L-proline]; m.p. 235°–237°. Recrystallization from methanol yields 1.52 g. of pure 1,1'-[dithiobis(D-2-methyl-1-oxopropane-3,1-diyl)]bis[L-proline]; m.p. 236°–237°.

(b)

1,1'-[Dithiobis(D-2-methyl-1-oxopropane-3,1-diyl)-]bis[L-proline], dibenzhydryl ester Diphenyldiazomethane (20.8 g., 107 mmol.) is added to methanolic solution (250 ml.) containing 12 g. (27.8 mmol.) of 1,1'-[dithiobis(D-2-methyl-1-oxopropane-3,1-diyl)]bis[L-proline]. The solution is stirred at room temperature overnight. The separated solid is filtered and dried to yield 18.7 g. of 1,1'-[dithiobis(D-2-methyl-1-oxopropane-3,1-diyl)]bis[L-proline], dibenzhydryl ester; m.p. 149°–152°; $[\alpha]_D^{25} = -188°$ (c=2, chloroform).

(c)

1-[3-Sulfenylphthalimido-2-D-methylpropanoyl]-L-proline, benzhydryl ester

Bromine (3.2 g., 20 mmol.) in 6 ml. of dichloroethane is added to an ice-cold solution of the dibenzhydryl ester product from part (b) (4.96 g., 6.5 mmol.) in 24 ml. of dichloroethane. The solution is stirred for three minutes and 4.96 g. (27 mmol.) of potassium phthalimide is added along with another 30 ml. of dichloroethane. After stirring in the ice-bath for fifteen minutes, the solution is stirred for 2.5 hours at room temperature. The solution is then centrifuged and the clear orange solution is evaporated and reevaporated from dichloroethane. The residue is dissolved in ethanol and concentrated to yield 5.2 g. of white crystalline 1-[3-sulfenylphthalimido-2-D-methylpropanoyl]-L-proline, benzhydryl ester; m.p. 142°–146° (dec. 141°); $[\alpha]_D^{25} = -95°$ (c=1, chloroform).

(d)

(S,S)-N-[3-[[3-(2-Carboxy-1-pyrrolidinyl)-2-methyl-3-oxopropyl]dithio]-N-(L-γ-glutamyl)-L-alanyl]glycine A mixture of glutathione (2.37 g., 7.7 mmole.) and 1-[3-sulfenylphthalimido-2-D-methylpropanoyl]-L-proline, benzhydryl ester (4.5 g., 8.5 mmol.) in 100 ml. of ethanol are refluxed for three hours. The solution is left overnight at room temperature. The separated solid is filtered off (4.4 g.) and the mother liquor evaporated (2.2 g.). Since both contain the desired product, they are deprotected separately using a mixture of trifluoroacetic acid (5 ml.), acetic acid (4 ml.), and anisole (1 ml.).

The deprotected product from the two reactions (3.3 g. and 0.9 g.) are combined along eith a 1.1 g. sample from an earlier small scale experiment. The total combined deprotected material (5.3 g.) is applied on a column of silica gel (mesh 60–200) built in n-butanol-acetic acid-water (4:1:1). The column is eluted with the same solvent system using gravity and the separation is repeated under moderate pressure for a fast column in the same system (silica gel, mesh 230–400). The fractions containing the desired product are pooled, evaporated, and the water soluble portion of this material is applied on a LH-20 column (2.5 cm.×110 cm.) built in water and eluted with water. 10 ml. fractions are collected and fractions 40–51 containing the desired product as a homogeneous material are pooled and lyophilized to yield 0.95 g. of (S,S)-N-[3-[[3-(2-carboxy-1-pyrrolidinyl)-2-methyl-3-oxopropyl]dithio]-N-(L-$\gamma$-glutamyl)-L-alanyl]glycine; $[\alpha]_d^{25} = -175°$ (c=1, water); $R_f$=0.2, n-butanol: acetic acid:water (4:1:1) on electrophoresis (2000 V, 25 minutes) in the pyridine-acetate pH 6.5 buffer it had a 130% mobility as that of aspartic acid.

Anal. Calc'd. for $C_{19}H_{30}N_4S_2$: C, 43.67; H, 5.79; N, 10.72; S, 12,27. $C_{19}H_{30}N_4S_2 \cdot 4H_2O$: C, 38.38; H, 6.44; N, 9.42; S, 10.78. Found: C, 38.44; H, 5.20; N, 9.59; S, 9.82.

EXAMPLES 2–35

Following the procedure of Example 1 but employing the α-amino acid of Col. I one obtains the product listed in Col. II.

| Example | Col. I | Col. II |
|---|---|---|
| 2 | 1-(3-mercaptopropanoyl)-L-proline | (S)-N-[3-[[3-(2-carboxy-1-pyrrolidinyl)-3-oxopropyl]dithio]-N-(L-γ-glutamyl)-L-alanyl]glycine |
| 3 | 1-(3-mercapto-2-D-methylpropanoyl)-4-hydroxy-L-proline | (S,S)-N-[3-[[3-(2-carboxy-4-hydroxy-1-pyrrolidinyl)-2-methyl-3-oxopropyl]dithio]-N-(L-γ-glutamyl)-L-alanyl]glycine |
| 4 | 1-(3-mercapto-2-D-trifluoromethyl-propanoyl)-L-proline | (S,S)-N-[3-[[3-(2-carboxy-1-pyrrolidinyl)-2-trifluoromethyl-3-oxopropyl]dithio]-N-(L-γ-glutamyl)-L-alanyl]glycine |
| 5 | 1-(3-mercapto-2-D-methylpropanoyl)-4-methyl-L-proline | (S,S)-N-[3-[[3-(2-carboxy-4-methyl-1-pyrrolidinyl)-2-methyl-3-oxopropyl]dithio]-N-(L-γ-glutamyl)-L-alanyl]glycine |
| 6 | 1-(3-mercapto-2-D-methylpropanoyl)-4-chloro-L-proline | (S,S)-N-[3-[[3-(2-carboxy-4-chloro-1-pyrrolidinyl)-2-methyl-3-oxopropyl]dithio]-N-(L-γ-glutamyl)-L-alanyl]glycine |
| 7 | 1-(3-mercaptopropanoyl)-4-fluoro-L-proline | (S)-N-[3-[[3-(2-carboxy-4-fluoro-1-pyrrolidinyl)-3-oxopropyl]dithio]-N-(L-γ-glutamyl)-L-alanyl]glycine |
| 8 | 1-(3-mercapto-2-D-methylpropanoyl)-4-phenoxy-L-proline | (S,S)-N-[3-[[3-(2-carboxy-4-phenoxy-1-pyrrolidinyl)-2-methyl-3-oxopropyl]dithio]-N-(L-γ-glutamyl)-L-alanyl]glycine |
| 9 | 1-(3-mercapto-2-D-methylpropanoyl)-4-phenylthio-L-proline | (S,S)-N-[3-[[3-(2-carboxy-4-phenylthio-1-pyrrolidinyl)-2-methyl-3-oxopropyl]dithio]-N-(L-γ-glutamyl)-L-alanyl]glycine |
| 10 | 1-(3-mercapto-2-D-trifluoromethylpropanoyl)-4-[[(4-methyl)phenyl]oxy]-L-proline | (S,S)-N-[3-[[3-(2-carboxy-4-[[(4-methyl)phenyl]oxy]-1-pyrrolidinyl]-2-trifluoromethyl-3-oxopropyl]dithio]-N-(L-γ-glutamyl)-L-alanyl]glycine |
| 11 | 1-(3-mercapto-2-D-methylpropanoyl)-4-methoxy-L-proline | (S,S)-N-[3-[[3-(2-carboxy-4-methoxy-1-pyrrolidinyl)-2-methyl-3-oxopropyl]dithio]-N-(L-γ-glutamyl)-L-alanyl]glycine |
| 12 | 1-(3-mercaptopropanoyl)-4-ethoxy-L-proline | (S)-N-[3-[[3-(2-carboxy-4-ethoxy-1-pyrrolidinyl)-3-oxopropyl]dithio]-N-(L-γ-glutamyl)-L-alanyl]glycine |
| 13 | 1-(3-mercapto-2-D-methylpropanoyl)-4-(1,1-dimethylethoxy)-L-proline | (S,S)-N-[3-[[3-(2-carboxy-4-(1,1-dimethylethoxy)-1-pyrrolidinyl]-2-methyl-3-oxopropyl]dithio]-N-(L-γ-glutamyl)-L-alanyl]glycine |
| 14 | 1-(3-mercapto-2-D-methylpropanoyl)-4-methylthio-L-proline | (S,S)-N-[3-[[3-(2-carboxy-4-methylthio-1-pyrrolidinyl)-2-methyl-3-oxopropyl]dithio]-N-(L-γ-glutamyl)-L-alanyl]glycine |
| 15 | 1-(3-mercapto-2-D-methylpropanoyl)-4-([1,1'-biphenyl]-4-yloxy)-L-proline | (S,S)-N-[3-[[3-[2-carboxy-4-([1,1'-biphenyl]-4-yloxy)-1-pyrrolidinyl]-2-methyl-3-oxopropyl]dithio]-N-(L-γ-glutamyl)-L-alanyl]glycine |
| 16 | 1-(3-mercapto-2-D-methylpropanoyl)-4-(2-naphthylenyloxy)-L- | (S,S)-N-[3-[[3-[2-carboxy-4-(2-naphthalenyloxy)-1-pyrrolidinyl]-2-methyl-3-oxopropyl]di- |

-continued

| Example | Col. I | Col. II |
|---|---|---|
| | proline | thio]-N-(L-γ-glutamyl)-L-alanyl]-glycine |
| 17 | 1-(3-mercapto-2-D-methylpropanoyl)-4-keto-L-proline | (S,S)-N-[3-[[3-(2-carboxy-4-keto-1-pyrrolidinyl)-2-methyl-3-oxopropyl]dithio]-N-(L-γ-glutamyl)-L-alanyl]-glycine |
| 18 | 1-(3-mercapto-2-D-methylpropanoyl)-4-[[(methylamino)carbonyl]oxy]-L-proline | (S,S)-N-[3-[[3-[2-carboxy-4-[[(methylamino)carbonyl]oxy]-1-pyrrolidinyl]-2-methyl-3-oxopropyl]dithio]-N-(L-γ-glutamyl)-L-alanyl]-glycine |
| 19 | 1-(3-mercapto-2-D-trifluoromethylpropanoyl)-4,4-dichloro-L-proline | (S,S)-N-[3-[[3-(2-carboxy-4,4-dichloro-1-pyrrolidinyl)-2-trifluoromethyl-3-oxopropyl]-dithio]-N-(L-γ-glutamyl)-L-alanyl]-glycine |
| 20 | 1-(3-mercapto-2-D-methylpropanoyl)-4,4-difluoro-L-proline | (S,S)-N-[3-[[3-(2-carboxy-4,4-difluoro-1-pyrrolidinyl)-2-methyl-3-oxopropyl]dithio]-N-(L-γ-glutamyl)-L-alanyl]glycine |
| 21 | 1-(3-mercapto-2-D-methylpropanoyl)-4,4-dimethoxy-L-proline | (S,S)-N-[3-[[3-(2-carboxy-4,4-dimethoxy-1-pyrrolidinyl)-2-methyl-3-oxopropyl]dithio]-N-(L-γ-glutamyl)-L-ananyl]-glycine |
| 22 | 1-(3-mercapto-2-D-methylpropanoyl)-4,4-dimethylthio-L-proline | (S,S)-N-[3-[[3-(2-carboxy-4,4-dimethylthio-1-pyrrolidinyl)-2-methyl-3-oxopropyl]dithio]-N-(L-γ-glutamyl)-L-alanyl]glycine |
| 23 | 1-(3-mercaptopropanoyl)-4,4-diethoxy-L-proline | (S)-N-[3-[[3-(2-carboxy-4,4-diethoxy-1-pyrrolidinyl)-3-oxopropyl]dithio]-N-[L-γ-glutamyl)-L-alanyl]glycine |
| 24 | 1-(3-mercapto-2-D-methylpropanoyl)-4,4-ethylenedioxy-L-proline | (S,S)-N-[3-[[3-(2-carboxy-4,4-ethylenedioxy-1-pyrrolidinyl)-2-methyl-3-oxopropyl]dithio]-N-(L-γ-glutamyl)-L-alanyl]-glycine |
| 25 | 1-(3-mercapto-2-D-methylpropanoyl)-4,4-ethylenedithio-L-proline | (S,S)-N-[3-[[3-(2-carboxy-4,4-ethylenedithio-1-pyrrolidinyl)-2-methyl-3-oxopropyl]dithio]-N-(L-γ-glutamyl)-L-alanyl]glycine |
| 26 | 1-(3-mercapto-2-D-methylpropanoyl)-4,4-trimethylenedioxy-L-proline | (S,S)-N-[3-[[3-(2-carboxy-4,4-trimethylenedioxy-1-pyrrolidinyl)-2-methyl-3-oxopropyl]-dithio]-N-(L-γ-glutamyl)-L-alanyl]glycine |
| 27 | 1-(3-mercapto-2-D-trifluoromethylpropanoyl)-4,4-ethylenedioxy-L-proline | (S,S)-N-[3-[[3-(2-carboxy-4,4-ethylenedioxy-1-pyrrolidinyl)-2-trifluoromethyl-3-oxopropyl]dithio]-N-(L-γ-glutamyl)-L-alanyl]glycine |
| 28 | 1-(3-mercapto-2-D-methylpropanoyl)-4,4-(1-methylethylenedioxy)-L-proline | (S,S)-N-[3-[[3-[2-carboxy-4,4-(1-methylethylenedioxy)-1-pyrrolidinyl]-2-methyl-3-oxopropyl]dithio]-N-(L-γ-glutamyl)-L-alanyl]glycine |
| 29 | 1-(3-mercapto-2-D-methylpropanoyl)-4,4-(phenylmethoxy)-L-proline | (S,S)-N-[3-[[3-[2-carboxy-4,4-(phenylmethoxy)-1-pyrrolidinyl]-2-methyl-3-oxopropyl]dithio]-N-(L-γ-glutamyl)-L-alanyl]glycine |
| 30 | 1-(3-mercapto-2-D-methylpropanoyl)-5-keto-L-proline | (S,S)-N-[3-[[3-(2-carboxy-5-keto-1-pyrrolidinyl)-2-methyl-3-oxopropyl]dithio]-N-(L-γ-glutamyl)-L-alanyl]glycine |
| 31 | 1-(3-mercapto-2-D-methylpropanoyl)-L-3,4-dehydroproline | (S,S)-N-[3-[[3-(2-carboxy-2,5-dihydro-1H-pyrrol-1-yl)-2-methyl-3-oxopropyl]dithio]-N-(L-γ-glutamyl)-L-alanyl]glycine |
| 32 | 3-(3-mercapto-2-D-methylpropanoyl)-4-L-thiazolidinecarboxylic acid | (S,S)-N-[3-[[3-(4-carboxy-3-thiazolidinyl)-2-methyl-3-oxopropyl]dithio]-N-(L-γ-glutamyl)-L-alanyl]glycine |
| 33 | 3-(3-mercapto-2-D-2-trifluoromethylpropanoyl)-4-L-thiazolidinecarboxylic acid | (S,S)-N-[3-[[3-(4-carboxy-3-thiazolidinyl)-2-trifluoromethyl-3-oxopropyl]dithio]-N-(L-γ-glutamyl)-L-alanyl]glycine |

-continued

| Example | Col. I | Col. II |
|---|---|---|
| 34 | 3-(3-mercapto-2-D-methylpropanoyl)-2-L-thiazolidinecarboxylic acid | (S,S)-N-[3-[[3-(2-carboxy-3-thiazolidinyl)-2-methyl-3-oxopropyl]dithio]-N-(L-γ-glutamyl)-L-alanyl]glycine |
| 35 | 3-(3-mercapto-2-D-methylpropanoyl)-2,2-dimethyl-4-L-thiazolidiencarboxylic acid | (S,S)-N-[3-[[3-(4-carboxy-2,2-dimethyl-3-thiazolidinyl)-2-methyl-3-oxopropyl]dithio]-N-(L-γ-glutamyl)-L-alanyl]glycine |

EXAMPLES 36–55

Following the procedure of Example 1 but substituting for the glutathione in part (d) the peptide shown below in Col. I, one obtains the product shown in Col. II.

Col. I $$\begin{array}{c} SH \\ | \\ CH_2 \\ | \\ A-NH-CH-CO-A_1 \end{array}$$

Col. II $$\begin{array}{c} CH_3 \quad H_2C\overset{CH_2}{\diagup}CH_2 \\ S-S-CH_2-CH-CO-N\quad\quad C-COOH \\ | \quad\quad\quad\quad\quad\quad\quad\quad\quad\quad | \;(L) \\ CH_2 \quad\quad\quad\quad\quad\quad\quad\quad\quad\;\; H \\ | \\ A-NH-CH-CO-A_1 \end{array}$$

| Example | A | A₁ |
|---|---|---|
| 36 | H₂N—CH—C(=O)— <br>     \|(L) <br> CH₂—CH₂—COOH | —NH—CH₂—COOH |
| 37 | H₂N—CH—C(=O)— <br>     \|(L) <br> CH₃ | —NH—CH₂—COOH |
| 38 | H₂N—CH—C(=O)— <br>     \|(L) <br> CH <br> H₃C⁄ \CH₃ | —NH—CH₂—COOH |
| 39 | H₂N—CH—C(=O)— <br>     \|(L) <br> CH₂ <br> \| <br> CH <br> H₃C⁄ \CH₃ | —NH—CH₂—COOH |
| 40 | H₂N—CH—C(=O)— <br>     \|(L) <br> CH₂—COOH | —NH—CH₂—COOH |
| 41 | H₂N—CH—CH₂—C(=O)— <br>     \|(L) <br> COOH | —NH—CH₂—COOH |
| 42 | H₂N—CH—C(=O)— <br>     \|(L) <br> CH₂—C₆H₅ | —NH—CH₂—COOH |

-continued

Col. I

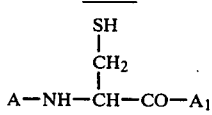

Col. II

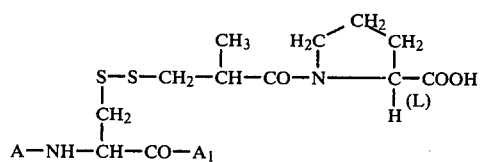

| Example | A | A₁ |
|---|---|---|
| 43 | H₂N—CH(L)—C(=O)—, CH₂—C₆H₄—OH | —NH—CH₂—COOH |
| 44 | H₂N—CH(L)—C(=O)—, CH₂-(indol-3-yl) | —NH—CH₂—COOH |
| 45 | H₂N—CH(L)—C(=O)—, (CH₂)₄—NH₂ | —NH—CH₂—COOH |
| 46 | H₂N—CH(L)—C(=O)—, (CH₂)₃NHC(=NH)NH₂ | —NH—CH₂—COOH |
| 47 | (L) proline residue HN—CH—C(=O)— (pyrrolidine) | —NH—CH₂—COOH |
| 48 | H₂N—CH₂—C(=O)— | —NH—CH₂—COOH |
| 49 | H₂N—CH₂—C(=O)— | —NH—CH(L)(COOH)—CH₂—CH₂—COOH |
| 50 | H₂N—CH₂—C(=O)— | —NH—CH(L)(CH₃)—COOH |
| 51 | H₂N—CH₂—C(=O)— | —NH—CH(L)(CH(CH₃)₂)—COOH |
| 52 | H₂N—CH₂—C(=O)— | (L) proline residue —N—CH—COOH |
| 53 | H₂N—CH(L)(COOH)—CH₂CH₂—C(=O)— | —NH—CH(L)(COOH)—CH₂—CH₂—COOH |
| 54 | H₂N—CH(L)(COOH)—CH₂CH₂—C(=O)— | —NH—CH(L)(CH₃)—COOH |

-continued

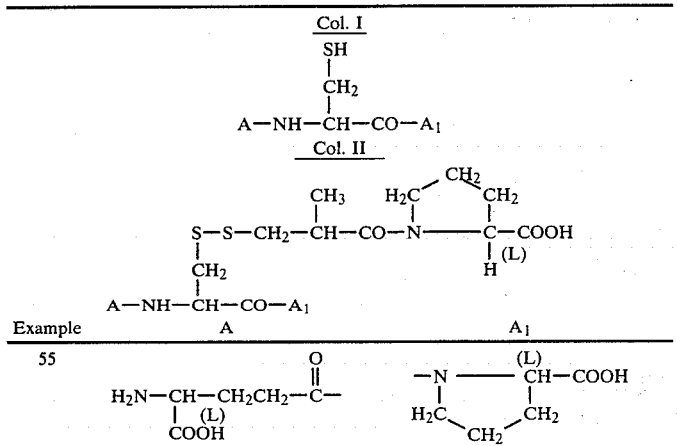

| Example | A | A₁ |
|---|---|---|
| 55 | H₂N—CH—CH₂CH₂—C(=O)— <br>           \|(L) <br>          COOH | —N—CH(L)—COOH (pyrrolidinyl ring) |

Similarly, by employing the peptides of Col. I with the α-imino acids shown in Col. I of Examples 2 to 35, other compounds within the scope of the invention are obtained.

EXAMPLE 56

(S,S)-N-[3-[[3-(2-Carboxy-1-pyrrolidinyl)-2-methyl-3-oxopropyl]dithio]-N-(L-γ-glutamyl)-L-alanyl]glycine, trisodium salt A solution of the product of Example 1 is treated with three equivalents of sodium bicarbonate and lyophilized to give (S,S)-N-[3-[[3-(2-carboxy-1-pyrrolidinyl)-2-methyl-3-oxopropyl]dithio]-N-(L-γ-glutamyl)-L-alanyl]glycine, trisodium salt.

In a similar manner, by employing potassium bicarbonate the corresponding tripotassium salt is obtained.

EXAMPLE 57

1000 tablets each containing the following ingredients:

| | | |
|---|---:|---|
| (S,S)-N-[3-[[3-(2-Carboxy-1-pyrrolidinyl)-2-methyl-3-oxopropyl]dithio]-N-(L-γ-glutamyl)-L-alanyl]glycine, trisodium salt | 100 | mg. |
| Corn starch | 50 | mg. |
| Gelatin | 7.5 | mg. |
| Avicel (microcrystalline cellulose) | 25 | mg. |
| Magnesium stearate | 2.5 | mg. |
| | 185 | mg. | are prepared (from sufficient bulk quantities) by mixing the (S,S)-[N-3-[[3-(2-carboxy-1-pyrrolidinyl)-2-methyl-3-oxopropyl]dithio]-N-(L-γ-glutamyl)-L-analyl]glycine, trisodium salt and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

EXAMPLE 58

An injectable solution is produced as follows:

| | | |
|---|---:|---|
| (S,S)-N-[3-[[3-(2-Carboxy-1-pyrrolidinyl)-2-methyl-3-oxopropyl]dithio]-N-(L-γ-glutamyl)-L-alanyl]glycine | 500 | g. |
| Methyl paraben | 5 | g. |
| Propyl paraben | 1 | g. |
| Sodium chloride | 25 | g. |
| Water for injection qs. | 5 | l. |

The active substance, preservatives and sodium chloride are dissolved in 3 liters of water and then the volume is brought up to 5 liters. The solution is filtered through a sterile filter and asceptically filled into presterilized vials which are then closed with presterilized rubber closures. Each vial contains 5 ml. of solution in a concentration of 100 mg. of active ingredient per ml. of solution for injection.

EXAMPLE 59

6000 tablets each containing the following ingredients:

| | | |
|---|---:|---|
| (S,S)-N-[3-[[3-(2-Carboxy-1-pyrrolidinyl)-2-methyl-3-oxopropyl]dithio]-N-(L-γ-glutamyl)-L-alanyl]glycine | 100 | mg. |
| Avicel (microcrystalline cellulose) | 100 | mg. |
| Hydrochlorothiazide | 12.5 | mg. |
| Lactose U.S.P. | 113 | mg. |
| Corn starch U.S.P. | 17.5 | mg. |
| Stearic acid U.S.P. | 7 | mg. |
| | 350 | mg. | are produced from sufficient bulk quantities by slugging the (S,S)-N-[3-[[3-(2-carboxy-1-pyrrolidinyl)-2-methyl-3-oxopropyl]dithio]-N-(L-γ-glutamyl)-L-alanyl]glycine, Avicel and a portion of the stearic acid. The slugs are ground and passed through a #2 screen, and then the hydrochlorothiazide, lactose, corn starch and remainder of the stearic acid. The mixture is compressed into 350 mg. capsule shaped tablets in a tablet press. The tablets are scored for dividing in half.

The products of Examples 2 to 55 can also be formulated according to the procedure of Examples 57 to 59.

What is claimed is:

1. A compound of the formula

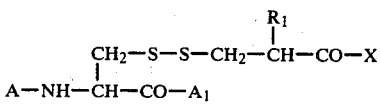

and salts thereof, wherein

A and $A_1$ are each amino acid residues independently selected from the group consisting of glycyl, alanyl, valyl, leucyl, α-glutamyl, γ-glutamyl, α-aspartyl, β-aspartyl, phenylalanyl, tyrosyl, lysyl, arginyl, and prolyl, said A residue being joined through a carbonyl group and said $A_1$ residue being joined through an amino group;

X is an α-imino acid residue selected from the group consisting of

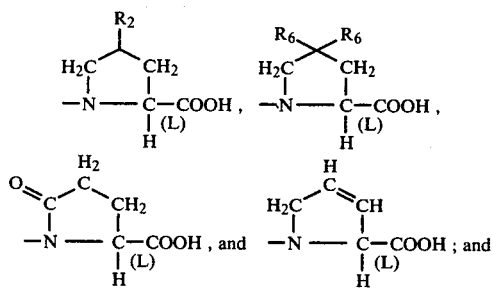

$R_2$ is hydrogen, hydroxy, lower alkyl, halogen, keto,

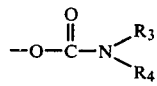

or $-Y-R_5$;

Y is O or S;

$R_5$ is lower alkyl, phenyl, phenyl-lower alkylene, 1- or 2-naphthyl, biphenyl, substituted phenyl, substituted phenyl-lower alkylene, substituted 1- or 2-naphthyl, or substituted biphenyl wherein said substituent is on the phenyl ring and is one or two members selected from the group consisting of lower alkyl or 1 to 4 carbons, lower alkoxy of 1 to 4 carbons, lower alkylthio of 1 to 4 carbons, chloro, fluoro, trifluoromethyl, acetyloxy, and hydroxy;

$R_6$ is halogen or $-Y-R_7$;

$R_7$ is lower alkyl, phenyl, phenyl-lower alkylene, substituted phenyl, or substituted phenyl-lower alkylene wherein said substituent is one or two members selected from the group consisting of lower alkyl of 1 to 4 carbons, lower alkoxy of 1 to 4 carbons, lower alkylthio of 1 to 4 carbons, chloro, fluoro, trifluoromethyl, acetyloxy, and hydroxy, or the $R_7$ groups join in an alkylene chain of 2 or 3 carbons to complete a 5- or 6-membered ring or said ring in which one of the carbon atoms has a lower alkyl or di(lower alkyl)substituent; and $R_3$ and $R_4$ are independently selected from the group consisting of hydrogen and lower alkyl.

2. A compound of claim 1 wherein $R_1$ is hydrogen, methyl, or trifluoromethyl;

A is γ-glutamyl;

$A_1$ is glycyl; and

X is (L)-proline, 4-hydroxy-(L)-proline, 4-methoxy-(L)-proline, 4,4-ethylenedioxo-(L)-proline, 4,4-ethylenedithio-(L)-proline, 4-phenoxy-(L)-proline, 4-phenylthio-(L)-proline, 4-(2-naphthylenyloxy)-(L)-proline, or 4-([1,1-biphenyl]-4-yloxy)-(L)-proline[, or (L)-thiazolidine-4-carboxylic acid].

3. A composition for treating hypertension comprising a pharmaceutically acceptable carrier and an effective amount of one or more hypotensive agents or pharmaceutically acceptable salts thereof of the formula

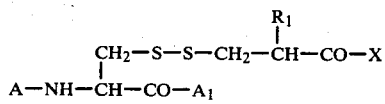

wherein

A and $A_1$ are each amino acid residues independently selected from the group consisting of glycyl, alanyl, valyl, leucyl, α-glutamyl, γ-glutamyl, α-aspartyl, β-aspartyl, phenylalanyl, tyrosyl, lysyl, arginyl, and prolyl, said A residue being joined through a carbonyl group and said $A_1$ residue being joined through an amino group;

X is an α-imino acid residue selected from the group consisting of

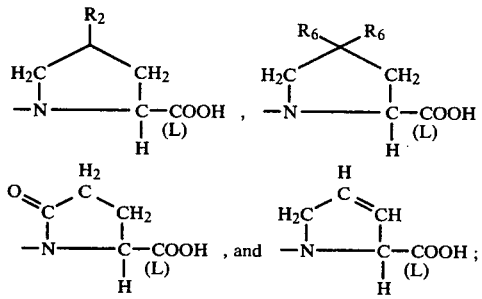

$R_2$ is hydrogen, hydroxy, lower alkyl, halogen, keto,

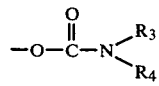

or $-Y-R_5$;

Y is O or S;

$R_5$ is lower alkyl, phenyl, phenyl-lower alkylene, 1- or 2-naphthyl, biphenyl, substituted phenyl, substituted phenyl-lower alkylene, substituted 1- or 2-naphthyl, or substituted biphenyl wherein said substituent is on the phenyl ring and is one or two members selected from the group consisting of lower alkyl of 1 to 4 carbons, lower alkoxy of 1 to 4 carbons, lower alkylthio of 1 to 4 carbons, chloro, fluoro, trifluoromethyl, acetyloxy, and hydroxy;

$R_6$ is halogen or $-Y-R_7$;

$R_7$ is lower alkyl, phenyl, phenyl-lower alkylene, substituted phenyl, or substituted phenyl-lower alkylene wherein said substituent is one or two members selected from the group consisting of lower alkyl of 1 to 4 carbons, lower alkoxy of 1 to 4 carbons, lower alkylthio of 1 to 4 carbons, chloro, fluoro, trifluoromethyl, acetyloxy, and hydroxy, or the $R_7$ groups join in an alkylene chain of 2 or 3 carbons to complete a 5- or 6-membered ring or said ring in which one of the carbon atoms has a lower alkyl or di(lower alkyl)substituent; and $R_3$ and $R_4$ are independently selected from the group consisting of hydrogen and lower alkyl.

4. The compound of claim 2 wherein $R_1$ is methyl and X is (L)-proline.

5. The compound of claim 4, (S,S)-N-[3-[[3-(2-carboxy-1-pyrrolidinyl)-2-methyl-3-oxopropyl]dithio]-N-(L-γ-glutamyl)-L-alanyl]glycine.

6. The composition of claim 3 wherein said hypotensive agent is (S,S)-N-[3-[[3-(2-carboxy-1-pyrrolidinyl)-2-methyl-3-oxopropyl]dithio]-N-(L-γ-glutamyl)-L-alanyl]glycine.

7. The composition of claim 3 also including a diuretic.

8. The method of alleviating hypertension which comprises administering an effective amount of the composition of claim 3.

* * * * *

UNITED STATES PATENT OFFICE
CERTIFICATE OF CORRECTION

PATENT NO. : 4,284,624
DATED : August 18, 1981
INVENTOR(S) : Sesha I. Natarajan, Miguel A. Ondetti, Shih-jung Lan, Keith K. Wong It is certified that error appears in the above-identified patent and that said Letters Patent are hereby corrected as shown below:

Col. 4, line 59, correct the spelling of "number".
Col. 7, line 2, correct the spelling of "with".

Col. 17, line 29 and col. 18, line 38, should read: -- $R_1$ is hydrogen, lower alkyl or halo substituted lower alkyl; --.

Signed and Sealed this

Sixth Day of April 1982

[SEAL]

Attest:

GERALD J. MOSSINGHOFF

Attesting Officer     Commissioner of Patents and Trademarks